(12) United States Patent
Mason et al.

(10) Patent No.: US 7,096,052 B2
(45) Date of Patent: Aug. 22, 2006

(54) OPTICAL PROBE INCLUDING PREDETERMINED EMISSION WAVELENGTH BASED ON PATIENT TYPE

(75) Inventors: Gene Mason, La Habra Heights, CA (US); Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 152 days.

(21) Appl. No.: 10/679,963

(22) Filed: Oct. 6, 2003

(65) Prior Publication Data

US 2004/0122302 A1    Jun. 24, 2004

Related U.S. Application Data

(60) Provisional application No. 60/416,492, filed on Oct. 4, 2002.

(51) Int. Cl.
*A61B 5/00* (2006.01)
(52) U.S. Cl. .................. 600/310; 600/323; 600/344
(58) Field of Classification Search ........ 600/322–323, 600/344, 310
See application file for complete search history.

(56) References Cited

U.S. PATENT DOCUMENTS

| | | | | |
|---|---|---|---|---|
| 4,380,240 A | * | 4/1983 | Jobsis et al. ............... | 600/344 |
| 4,802,485 A | * | 2/1989 | Bowers et al. ............. | 600/324 |
| 5,099,842 A | * | 3/1992 | Mannheimer et al. ...... | 600/323 |
| 5,237,994 A | * | 8/1993 | Goldberger ............... | 600/323 |
| 5,337,744 A | | 8/1994 | Branigan | |
| 5,452,717 A | | 9/1995 | Branigan et al. | |
| 5,490,505 A | | 2/1996 | Diab et al. | |
| 5,632,272 A | | 5/1997 | Diab et al. | |
| 5,638,818 A | | 6/1997 | Diab et al. | |
| 5,645,440 A | | 7/1997 | Tobler et al. | |
| 5,685,299 A | | 11/1997 | Diab et al. | |
| 5,769,785 A | | 6/1998 | Diab et al. | |
| 5,772,587 A | * | 6/1998 | Gratton et al. ............. | 600/323 |
| 5,782,757 A | | 7/1998 | Diab et al. | |
| 5,813,980 A | * | 9/1998 | Levinson et al. .......... | 600/338 |
| 5,830,137 A | * | 11/1998 | Scharf ....................... | 600/323 |
| 5,934,925 A | | 8/1999 | Tobler et al. | |
| 6,002,952 A | | 12/1999 | Diab et al. | |
| 6,036,642 A | | 3/2000 | Diab et al. | |
| 6,061,584 A | * | 5/2000 | Lovejoy et al. ............ | 600/344 |
| 6,067,462 A | | 5/2000 | Diab et al. | |
| 6,081,735 A | | 6/2000 | Diab et al. | |
| 6,088,607 A | | 7/2000 | Diab et al. | |
| 6,157,850 A | | 12/2000 | Diab et al. | |
| 6,184,521 B1 | | 2/2001 | Coffin, IV et al. | |
| 6,206,830 B1 | | 3/2001 | Diab et al. | |
| 6,236,872 B1 | | 5/2001 | Diab et al. | |
| 6,256,523 B1 | | 7/2001 | Diab et al. | |
| 6,263,222 B1 | | 7/2001 | Diab et al. | |
| 6,280,213 B1 | | 8/2001 | Tobler et al. | |
| 6,334,065 B1 | | 12/2001 | Al-Ali et al. | |
| 6,388,240 B1 | | 5/2002 | Schulz et al. | |
| 6,397,091 B1 | | 5/2002 | Diab et al. | |
| 6,501,975 B1 | | 12/2002 | Diab et al. | |
| 6,541,756 B1 | | 4/2003 | Schulz et al. | |
| 6,580,086 B1 | | 6/2003 | Schulz et al. | |

(Continued)

*Primary Examiner*—Eric F. Winakur
(74) *Attorney, Agent, or Firm*—Knobbe, Martens, Olson & Bear LLP

(57) ABSTRACT

A reflectance sensor which can be applied to a patient in a manner which reduces the light energy reaching the detector without first being attenuated by the tissue at the measurement site. Moreover, the reflectance sensor includes emitting devices adapted for use in legacy patient monitoring systems.

16 Claims, 3 Drawing Sheets

U.S. PATENT DOCUMENTS 6,584,336 B1 6/2003 Ali et al.
6,606,511 B1 8/2003 Ali et al.
6,650,917 B1 11/2003 Diab et al.
6,684,090 B1 1/2004 Ali et al.
6,748,254 B1 * 6/2004 O'Neil et al. ............... 600/344

* cited by examiner

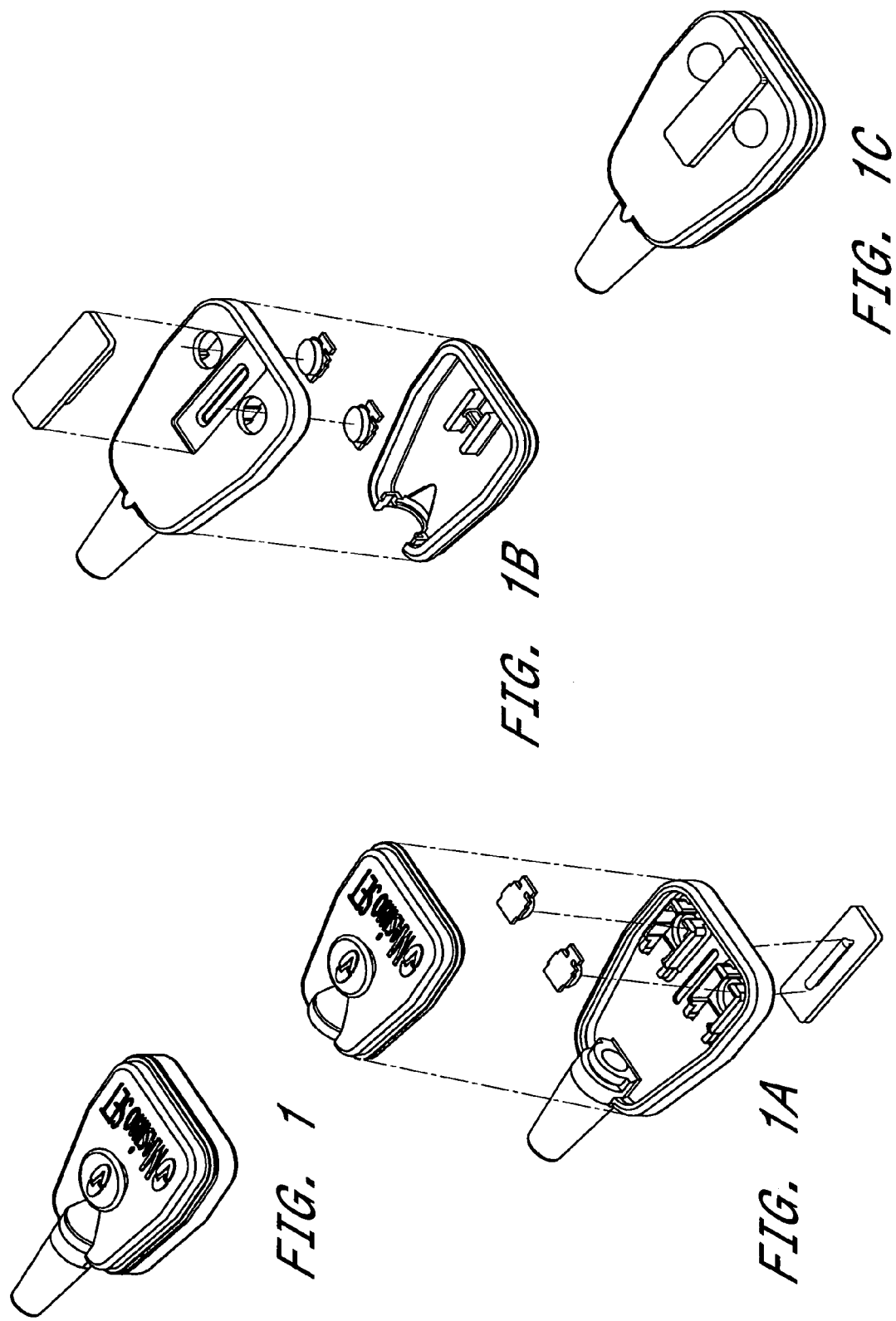

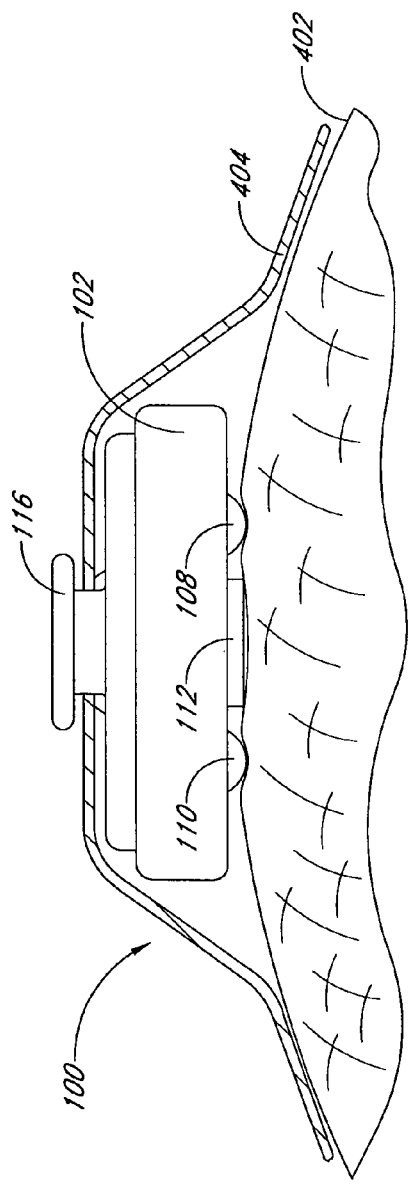
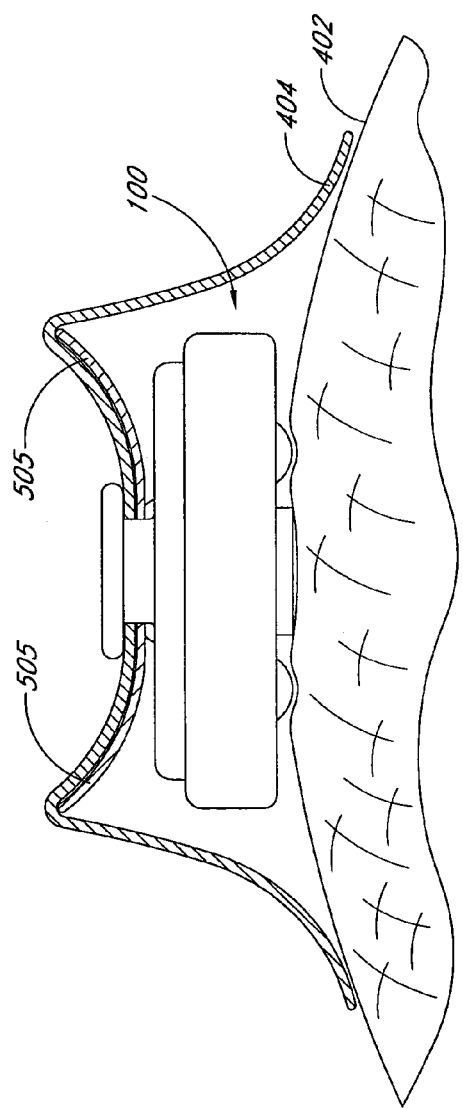

OPTICAL PROBE INCLUDING PREDETERMINED EMISSION WAVELENGTH BASED ON PATIENT TYPE

RELATED APPLICATIONS

The present application claims priority to U.S. Provisional Application No. 60/416,492, filed Oct. 4, 2002.

FIELD OF THE INVENTION

The present invention relates to the field of optical sensors. More specifically, the invention relates to reflectance optical sensors.

BACKGROUND OF THE INVENTION

Pulse oximetry is a non-invasive procedure for determining physiological parameters, such as an oxygen saturation level of arterial blood, pulse rate or the like, by processing received light-energy emissions after they have been attenuated by tissue at a measurement site. Generally, pulse oximetry involves an optical probe or sensor comprising one or more emitters, such as light emitting diodes (LEDs), and a photodetector (detector). The LEDs and detector are positioned in proximity with the patients skin. The LEDs emit light energy at predetermined wavelengths which transmits through the patient's tissue, is attenuated thereby, and is detected by the detector. A signal representative of the detected attenuated light energy is then passed through electrical communication to a monitor, such as a pulse oximeter, which processes the signal and determines one or more physiological parameters of the tissue at the measurement site.

Optical probes are generally applied to the measurement site in at least several distinctive manners. For example, one application positions the emitters on a side of the measurement site opposite the detector such that the light energy passes from one side of the measurement site, through the tissue, and to the detector positioned on the other side of the measurement site. Another reflective-type application positions the emitter and detector generally proximate one another on the same side of the measurement site. Drawbacks arise in reflectance-type sensors when light energy from the LEDs bounces along the surface of the tissue at the measurement site, or otherwise reaches the detector without passing through the tissue. Such light energy has not been attenuated by the tissue, and therefore, distorts or otherwise provides noise to the energy being received at the detector.

Additionally, reflectance-type sensors present various drawbacks during application, such as, for example, improper positioning on a measurement site, improper securement to the same, or the like. These drawbacks can increase the likelihood that light energy reaches the detector without having first been attenuated by the tissue.

Monitoring systems can also present drawbacks of backwards compatibility when dealing with newly developed sensor technologies. For example, pulse oximeters generally include sets of calibration curves used to associate data received from the detector with values of data used to determine the physiological parameters or the parameters themselves. Thus, as new sensors are developed and used during patient monitoring, the oximeter may not include an appropriate set of calibration curves to appropriately associate detected energy with the foregoing data.

Embodiments of the present invention seek to overcome some or all of these and other problems.

SUMMARY OF THE INVENTION

Therefore, a need exists for a reflectance-type sensor (reflectance sensor) which can be applied to a patient in a manner which reduces the light energy reaching the detector without first being attenuated by the tissue at the measurement site. Additionally, a need exists for accurately employing new sensors, such as the reflectance sensor, in legacy patient monitoring devices, such as oximeter systems already in use. Accordingly, aspects of the invention include a reflectance sensor which can be applied to a patient in a manner which reduces the light energy reaching the detector without first being attenuated by the tissue at the measurement site. Other aspects include deployment of the sensor in a manner which is compatible with legacy oximeter systems.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements. In addition, the first digit of each reference number indicates the figure in which the element first appears.

FIGS. 1–1B illustrate an exemplary assembled reflectance sensor and exemplary exploded perspective views of the reflectance sensor, respectively, according to embodiments of the invention.

FIG. 1C illustrates a tissue-side perspective view the assembled reflectance sensor of FIG. 1, according to an embodiment of the invention.

FIG. 4 illustrates a side view of the reflectance sensor of FIG. 1 attached to a measurement site, according to an embodiment of the invention.

FIG. 5 illustrates a side view of the reflectance sensor of FIG. 1 attached to a measurement site, according to another embodiment of the invention.

DETAILED DESCRIPTION OF THE PREFERRED EMBODIMENT

Figure 2A:
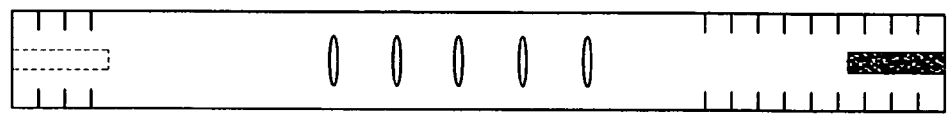
FIGS. 2A and 2B illustrate a wrap for attaching the reflectance sensor of FIG. 1, according to an embodiment of the invention.

Aspects of the invention include a reflectance sensor including protruding lenses and a protruding optical barrier. According to one embodiment, one lens houses the one or more emitters and the other lens houses the detector. In addition, the reflectance sensor includes an attachment mechanism which provides sufficient pressure holding the sensor against a measurement site such that the protruding lenses and optical barrier noninvasively recess into the tissue of the measurement site. Thus, when the emitter emits light energy through a first lens recessed into the tissue, the light energy enters the tissue, is attenuated, and is received by the second lens recessed into the tissue and housing the detector.

The recessed optical barrier advantageously reduces a potential that the light energy can reach the second lens and then the detector without first being attenuated by the tissue.

According to one embodiment, the attachment mechanism comprises a wrap such as a headband, having an adjustment assembly, such as hook-and-loop material. Adjustment of the adjustment assembly advantageously adjusts the pressure exerted by the sensor against the measurement site. According to another embodiment, the attachment mechanism comprises an adhesive tape. In yet another embodiment, the attachment mechanism or the sensor may include a biasing member biased to apply additional force against the sensor toward the measurement site, thereby advantageously increasing the pressure on the same.

In yet another embodiment, the emitter emits light energy at wavelengths other than those expected by the legacy oximeter system. For example, the emitter can emit light energy at wavelengths chosen such that use of the legacy set of calibration curves by the oximeter system advantageously produces accurate data.

To facilitate a complete understanding of the invention, the remainder of the detailed description describes the invention with reference to the drawings.

FIGS. 1A and 1B illustrate exploded perspective views of a reflectance sensor 100 according to an embodiment of the invention. As shown in FIGS. 1A and 1B, the sensor 100 includes a housing 102, comprising a top portion 104 and a bottom portion 106, a first lens 108 housing one or more light energy emission devices such as LEDs, a second lens 110 housing one or more detectors, and an optical barrier 112. According to one embodiment, the housing 102 positions the first and second lenses, 108 and 110, proximate one another, with the optical barrier 112 in between, such that each protrudes from a tissue-facing surface 114 thereof. For example, as shown in FIGS. 1A and 1B, the bottom portion 106 of the housing 102 includes apertures and mounting structures matchable with the first and second lenses, 108 and 110, and the optical barrier 112, to position the same to protrude from the surface 114.

According to an embodiment, the housing 102 comprises a pliable material such as Santoprene™, another thermoplastic elastomer (TPE), silicone, or the like. The upper portion 104 of the housing 102 includes a positioning member 116, such as, for example, a button-style positioning member. For example, the positioning member 116 comprise a structure or receives a structure from an attachment mechanism for attaching the sensor 100 to a measurement site. Use of the positioning member will be disclosed in greater detail with reference to FIGS. 2–4.

An exemplary embodiment of assembled sensor 100 shown in FIG. 1C, which illustrates the first and second lenses, 108 and 110, and the optical barrier 112, protruding from surface 114 such that when the sensor 100 is attached to a measurement site, the lenses, 108 and 110, and the optical barrier 112, noninvasively recess into the tissue such that light energy from the emitter of the first lens 108 is less likely to reach the second lens 110 without being attenuated by tissue of the measurement site.

According to one embodiment, the first and second lenses, 102 and 104, comprise an about 0.200 inch diameter cylinder with an about 0.020 inch think flange made of clear silicone or another suitable material, and includes a radius of about 0.100 inches to about 0.150 inches, and preferably about 0.125 inches.

Moreover, each lens protrudes through the surface 114 approximately about 0.050 inches, but could protrude from approximately about 0.025 inches to about 0.075 inches.

In one embodiment, the emitters emit light energy at wavelengths other than those expected by the legacy oximeter system. For example, the emitter can emit light energy at wavelengths chosen such that use of the legacy set of calibration curves by the oximeter system advantageously produces accurate data. For example, a caregiver may receive instructions for choosing a particular sensor from a group of sensors 100 based on, for example, the type of patient being monitored, the measurement site, the type of oximeter, or the like. According to one embodiment, the sensors 100 may include at least one emitter emitting light energy at wavelengths ranging throughout those useful in patient monitoring, such as from the visible red to infrared. More specifically, the sensors 100 may include an emitter emitting light energy at wavelengths ranging from about 650 nm to about 660 nm. Even more specifically, the sensors 100 may include an emitter emitting light energy at wavelengths of about 654 nm.

According to an embodiment, the optical barrier 112 comprises an about 0.050 inch thick black TPE strip about 0.240 inches wide and protrudes through the surface 114 approximately about 0.020 inches. However, the optical barrier 112 could protrude from approximately about 0.010 inches to about 0.040 inches. Also, the optical barrier 112 may advantageously be a integral portion of the housing 102.

Although the sensor 100 is disclosed with reference to its preferred embodiment, the invention is not intended to be limited thereby. Rather, a skilled artisan will recognize from the disclosure herein a wide number of alternatives for the sensor 100. For example, the sensor 100 may include flex circuitry, may include plastic or other fixed-form material, may terminally end in a cable adapter configured to receive a mating end of a patient cable connected to, for example, an oximeter, may include belt-loop protrusions configured to threadably receive an attachment mechanism, snaps, combinations of the same, or the like.

Figure 2B:
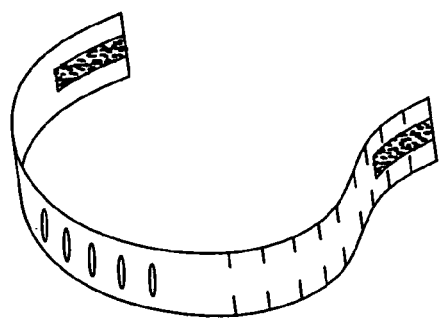

FIGS. 2A and 2B illustrate an attachment mechanism comprising a wrap 202 for attaching the reflectance sensor 100 to the measurement site, according to an embodiment of the invention. As shown in FIGS. 2A and 2B, the wrap 202 includes an adjustment assembly 204 for adjusting the wrap 202 to form fit, for example, around the measurement site. According to one embodiment, the assembly 204 comprises hook-and-loop material such as Velcro®, however, the assembly 204 may comprise any suitable asssembly adapted to adjustably encompass the measurement site. FIGS. 2A and 2B also illustrate the wrap 202, such as a headband, including button hole style slots 206 configured to receive the positioning member 116 of the sensor 100. Moreover, the wrap 200 includes indicia 208, such as ruler-style markings, for indicating the application of appropriate pressure. For example, according to one embodiment, the sensor 100 is attached to the wrap 202 by pushing the positioning member 116 through an appropriate slot 206. The headband can then be applied to a patient in a friction fit manner. According to one embodiment, a caregiver can then tighten the headband, for example, a predetermined number of indicia 208, to ensure sufficient pressure is applied to the sensor 100 to press the lenses 108 and 110 noninvasively into the tissue of the measurement site.

Figure 3:
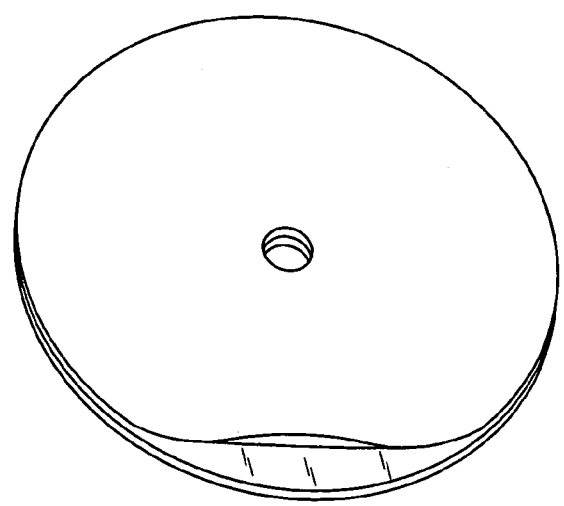
FIG. 3 illustrates a tape for attaching the reflectance sensor of FIG. 1, according to an embodiment of the invention.

FIG. 3 illustrates an attachment mechanism comprising a tape 302 for attaching the reflectance sensor 100 to the measurement site, according to an embodiment of the invention. As shown in FIG. 3, the tape 302 comprises an adhesive tape of any suitable shape designed to substantially fix the sensor 100 to the tissue of the measurement site. According to one embodiment, the tape 302 may include an adhesive side initially protected by a release liner layer 304. Additionally, the tape 302 may include a slot 306 adapted to advantageously receive the positioning member 116, thereby potentially providing a caregiver with a choice of attachment mechanism for the sensor 100, depending upon, for example, the type and condition of the tissue at the measurement site.

FIG. 4 illustrates a side view of the reflectance sensor 100 attached to a measurement site 402, according to an embodiment of the invention. As shown in FIG. 4, an attachment mechanism 404, such as, for example, the wrap 202 or the tape 302, applies pressure to the sensor 100 pushing the lenses 108 and 110 and the optical barrier 112 into the tissue of the site 402. Similarly, FIG. 5 illustrates a side view of the reflectance sensor 100 attached to the measurement site 402, according to another embodiment of the invention. As shown in FIG. 5, an additional pressure applicator 502, such as a biasing member, is included to apply and focus pressure against the sensor 100. In one embodiment, the pressure application 502 comprises a flexible convex member having structural memory such that after distortion, the member exerts force attempting to return to its original shape. Thus, when the pressure applicator 502 is included within the attachment mechanism 404 or as a part of the sensor 100, pressure can be more narrowly focused against the sensor 100.

Although the sensor 100 and the attachment mechanism 404 have been disclosed with reference to their preferred embodiment, the invention is not intended to be limited thereby. Rather, a skilled artisan will recognize from the disclosure herein a wide number of alternatives either or both of the sensor 100 and the attachment mechanism 404. For example, the wrap 202 may comprise a foot band, or the attachment mechanism 404 may comprise any suitable adjustable structure such as structures adapted to cooperate with, for example, the positioning member 116 of the sensor 100. Additionally, the surface 114 can include adhesive or the like.

Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

What is claimed is:

1. An optical probe capable of outputting a signal indicative of light transmitted through body tissue, the optical probe comprising:
   one or more emitters capable of emitting light;
   detector circuitry capable of detecting light transmitted through body tissue of a patient and outputting a signal usable to determine at least one physiological parameter of the patient;
   a substantially rigid probe housing including a substantially planar lens side, wherein said probe housing houses the one or more emitters and the detector circuitry;
   a single substantially circular substantially convex emitter lens protruding a distance from the probe housing;
   a single substantially circular substantially convex detector lens protruding about the distance from the probe housing; and
   a protruding optical barrier protruding from the probe housing substantially along an axis perpendicular to a line connecting the single emitter lens and the singal detector lens, wherein the optical barrier is positioned to reduce an amount of emitted light capable of reaching the detector circuitry without being transmitted through body tissue, wherein only the single emitter lens, the single detector lens, and the optical barrier protrude from the substantially planar lens side of the probe housing, thereby reducing an amount of protruding structure recessing into the body tissue of the patient.

2. The optical probe of claim 1, wherein the emitter lens protrudes a range of about 0.025 to about 0.075 inches.

3. The optical probe of claim 2, wherein the emitter lens protrudes about 0.050 inches.

4. The optical probe of claim 1, wherein the detector lens protrudes a range of about 0.010 to about 0.040 inches.

5. The optical probe of claim 4, wherein the detector lens protrudes about 0.020 inches.

6. The optical probe of claim 1, wherein one of the one or more emitters emits light at a wavelength unexpected by an oximeter communicating with said optical probe, and wherein said unexpected wavelength causes the oximeter to determine more accurate values for said at least one physiological parameter.

7. The optical probe of claim 6, wherein said unexpected wavelength ranges from about 650 to about 660 nanometers.

8. The optical probe of claim 7, wherein said unexpected wavelength comprises about 654 nanometers.

9. The optical probe of claim 1, wherein the probe housing further comprises a first positioning member and wherein said optical probe further comprises an attachment mechanism including at least one second positioning member mechanically mateable with the first positioning member to position the probe housing with respect to the attachment mechanism, wherein attachment of the attachment mechanism to the body tissue positions the probe housing against the body tissue with sufficient pressure to noninvasively recess the protruding optical barrier, the protruding emitter lens and the protruding detector lens into the body tissue substantially along a plane thereof.

10. The optical probe of claim 9, wherein the attachment mechanism further comprises a pressure applicator capable of applying sufficient pressure against the probe housing to assist the attachment mechanism in accomplishing the noninvasive recessing.

11. The optical probe of claim 10, wherein the pressure applicator comprises a substantially convex biasing member.

12. The optical probe of claim 9, wherein the attachment mechanism comprises a headband.

13. The optical probe of claim 12, wherein the headband further comprises:
   a plurality of the second positioning members, each member mechanically mateable with the first positioning member to provide for a plurality of potential positions of the probe housing with respect to the attachment mechanism; and
   indicia on the headband instructing a caregiver which of the potential positions will apply a predetermined amount of pressure against the probe housing.

14. The optical probe of claim 13, wherein the indicia include ruler-like indicia.

15. The optical probe of claim 9, wherein the attachment mechanism comprises an adhesive tape.

16. The optical probe of claim 15, wherein the second positioning member is substantially centered with respect to the adhesive tape.

* * * * *

UNITED STATES PATENT AND TRADEMARK OFFICE
CERTIFICATE OF CORRECTION

| | | |
|---|---|---|
| PATENT NO. | : 7,096,052 B2 | Page 1 of 1 |
| APPLICATION NO. | : 10/679963 | |
| DATED | : August 22, 2006 | |
| INVENTOR(S) | : Mason et al. | |

It is certified that error appears in the above-identified patent and that said Letters Patent is hereby corrected as shown below:

Page 2, column 2 Item [56] (U.S. Patent Documents), line 2, after "6,748,254" delete "B1" and insert -- B2 --, therefore.

At column 2, line 37, after "view" insert -- of --.

At column 3, line 61, after "inch" delete "think" and insert -- thick --, therefore.

At column 4, line 25, before "integral" delete "a" and insert -- an --, therefore.

At column 4, line 46, delete "asssembly" and insert -- assembly --, therefore.

At column 5, line 66, in Claim 1, delete "singal" and insert -- single --, therefore.

Signed and Sealed this

Twelfth Day of June, 2007

JON W. DUDAS
*Director of the United States Patent and Trademark Office*